(12) United States Patent
Kopetzki et al.

(10) Patent No.: US 6,391,571 B1
(45) Date of Patent: May 21, 2002

(54) RECOMBINANT INACTIVE AVIDIN MUTANTS

(75) Inventors: Erhard Kopetzki; Rainer Müller, both of Penzberg; Richard Engh, München; Urban Schmitt, Oberhausen; Arno Deger, Pernzberg; Hans Brandstetter, Chelsea, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/366,862

(22) Filed: Aug. 4, 1999

Related U.S. Application Data

(62) Division of application No. 08/831,399, filed on Apr. 1, 1997.

(51) Int. Cl.$^7$ .................. G01N 33/53; C07K 14/00; A61K 38/00
(52) U.S. Cl. .................. 435/7.5; 435/7.1; 530/350; 530/300; 514/12
(58) Field of Search .................. 435/7.1, 7.5; 530/350, 530/300; 514/12

(56) References Cited

U.S. PATENT DOCUMENTS

| 5,041,378 A | 8/1991 | Drummond et al. |
| 5,686,268 A | 11/1997 | Alila et al. |
| 5,728,803 A | 3/1998 | Urfer et al. |

FOREIGN PATENT DOCUMENTS

| IL | WO-2001005977 A1 * | 1/2001 |
| WO | WO 9624606 | 8/1996 |
| WO | WO 9700329 | 1/1997 |

OTHER PUBLICATIONS

Martilla et al, "Recombinant NeutraLite Avidin: a non–glycosylated, acidic mutant of chicken avidin that exhibits high affinity for biotin and low non–specific binding properties," Feb. 04, 2000, FEBS Letters, vol. 467, pp 31–36.*

Laitnen et al. "Mutationof a critical tryptophan to lysine in avidin or streptavidin may explain why sea urchin fibropellin adopts an avidin–like domain," Nov. 12, 1999, FEBS Letters, vol. 461, pp. 52–58.*

Nardone et al. "Biochemical characterization and crystal structure of a recombinant hen avidin and its acidic mutant expressed in *Escherichia coli*," Sep. 01, 1998, Europ. J. of Biochem., vol. 256 (2), pp. 453–460.*

Sano, et al, "Molecular Engineering of Streptavidin," Ann. NY Acad. Sci 799:383–390 (1996).

Sano, et al, "Intersubunit contacts made by tryptophan 120 with biotin are essential for both strong biotin binding and biotin–induced tighter subunit association of Streptavidin," Proc. Natl. Acad. Sci USA 92:3180–3184 (1995).

Chilkoti, et al, "Engineered Chimeric Streptavidin Tetramers As Novel Tools For Bioseparations And Drug Delivery," Biotechnology 13:1198–1204 (1995).

Carter, "Site specific Proteolysis of Fusion Proteins," ACS Symp. Ser 427: 181–193 (1990).

Gitlin, et al, "Studies on the biotin—binding sites of avidin and streptavidin," Biochem J 269:527–536 (1990).

Weber, et al, "Structural Origins of High Affinity Biotin binding to Streptavidin" Science 243:85–88 (1989).

Bell, et al, "Proteins and Enzymes," (Prentice Hall, 1988), p. 61.

* cited by examiner

Primary Examiner—Karen Cochrane Carlson
Assistant Examiner—Rita Mitra

(57) ABSTRACT

The present invention concerns muteins of avidin and streptavidin with a reduced binding affinity for biotin as well as their use as interference elimination reagents in methods for the determination of an analyte e.g. in diagnostic tests such as for example immunoassays and nucleic acid hybridization assays. In addition the invention concerns the use of muteins of avidin and streptavidin as systems capable of regeneration for binding biotin e.g. for the analysis of biotinylated molecules, for examining receptor ligand interactions as well as for the affinity purification of biotinylated molecules.

24 Claims, 1 Drawing Sheet

RECOMBINANT INACTIVE AVIDIN MUTANTS

Figure 1:
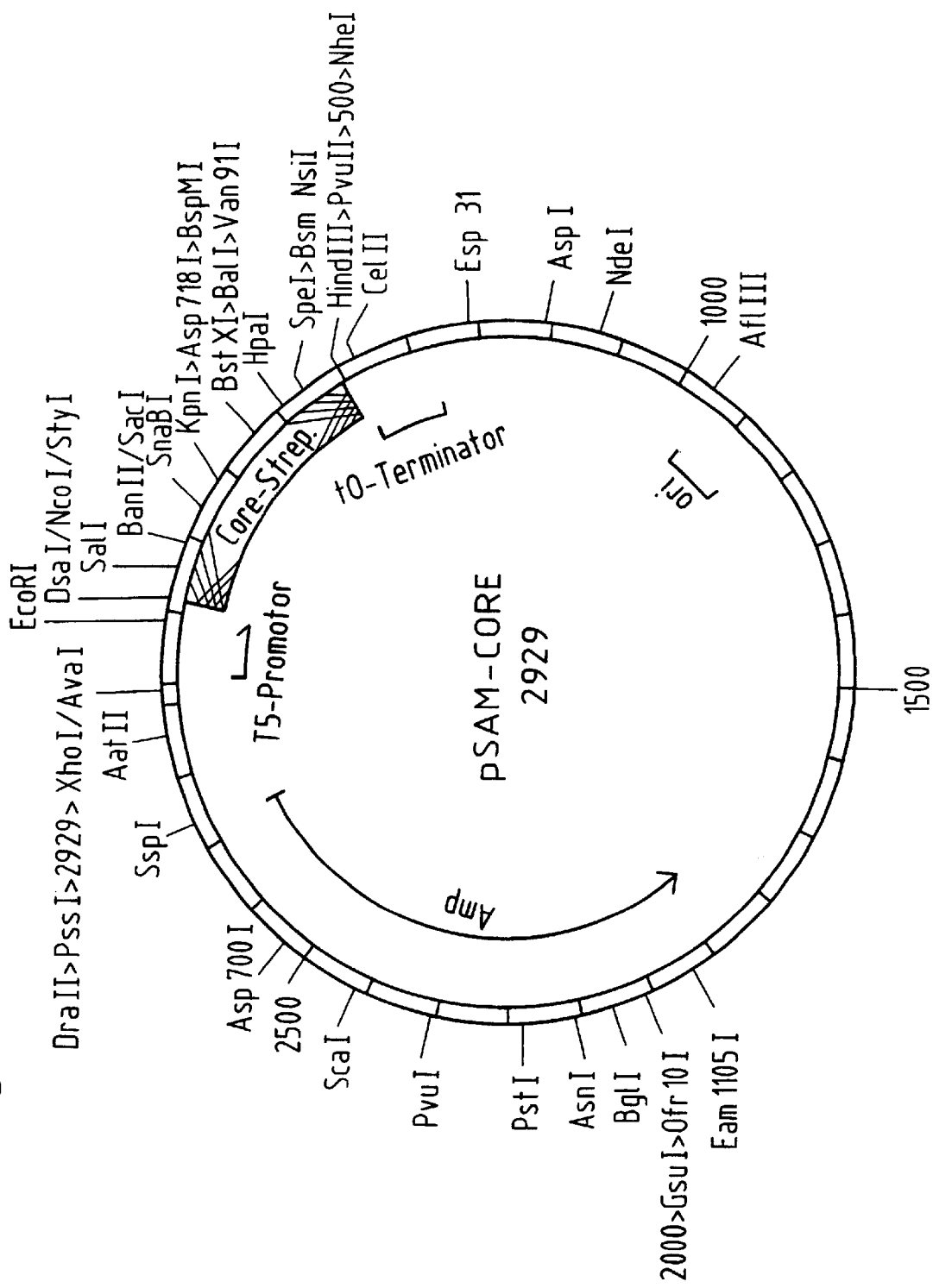

This application is a Division of Ser. No. 08/831,399 filed on Apr. 1, 1997.

The present invention concerns muteins of avidin and streptavidin with a reduced binding affinity for biotin as well as their use as interference elimination reagents in methods for the determination of an analyte e.g. in diagnostic tests such as immunoassays and nucleic acid hybridization assays. In addition the invention concerns the use of muteins of avidin and streptavidin as systems that can be regenerated for binding biotin for example for the analysis of biotinylated molecules, for investigating receptor-ligand interactions as well as for the affinity purification of biotinylated molecules.

In detection methods for the determination of analytes such as immunoassays and nucleic acid hybridization assays the analytes are often determined by means of high affinity interaction between the partners of a specific binding pair. A typical example for a specific binding pair is the avidin/streptavidin-biotin complex. When using the avidin/streptavidin-biotin binding pair its high binding affinity is used. In this process a solid phase coated with avidin/streptavidin is for example used to which a biotinylated complex of analyte and specific receptor can bind. In other test formats avidin/streptavidin can also be used in a soluble form.

However, apart from specific interactions. side reactions often also occur such as for example undesired interactions and unspecific binding reactions between the test components and additional components present in the sample or on the solid phase. In particular other substances present in the sample often bind to immobilized or soluble avidin and streptavidin and thereby cause false positive or false negative test results. Furthermore these interactions can also cause an increase in the background signal and an increased scattering of the signals which decreases the sensitivity and specificity of the respective test.

Various attempts have been made to reduce these unspecific interactions. Thus it is for example known that various carbohydrate components and various proteins, protein mixtures or protein fractions and their hydrolysates can reduce unspecific interactions between the test components and the analyte in immunoassays (Robertson et al., J. of Immun. Med. 26 (1985) 195; EP-A-260 903; U.S. Pat. No. 4,931,385). However, the use of such carbohydrate and protein components has the disadvantage that components contained therein can cause additional interferences in the test. Enzymatically produced hydrolysates can in addition be contaminated by proteases used in their production and as a rule do not have a uniform quality since the cleavage is difficult to control. Such protease impurities can attack test components and already in small amounts lead to impairment of test function and storage stability.

Furthermore the use of chemically modified proteins especially of succinylated or acetylated proteins (U.S. Pat. No. 5,051,356; EP-A-0 525 916) has also been described to reduce unspecific interactions. However, it is not possible with these substances to avoid many of the false positive or false negative results in tests for antibodies from serum.

In order to avoid unspecific interactions it has additonally been proposed that ultrafine particles be added to the test reagents with a maximum average size of 0.2 $\mu$m which are formed in such a way that they bind to interfering components and capture them (EP 0 163 312). However, this requires a special preparation of these ultrafine particles and in addition the type of unspecific factors present in the sample must be known.

In DE-A-44 07 423 and DE-A-44 34 093 it has been proposed that interferences which occur due to unspecific interactions between sample components and a streptavidin-coated solid phase be eliminated by means of a pre-reaction. The pre-reaction is advantageously carried out on a solid phase which is as similar as possible to the active streptavidin-coated solid phase but to which the sample molecules cannot bind specifically. In contrast unspecific components also bind to the inactive solid phase and can therefore be removed.

According to DE-A-44 07 423 streptavidin can be inactivated by covalent derivatization or covalent modification. However, a disadvantage is that this requires a time-consuming subsequent chemical modification. Moreover, chemical derivatization can change the region around the active centre of the native streptavidin in an undesired manner which reduces the interference elimination effects and may even lead to additional interfering interactions. Interference by unspecific interactions which occur at the biotin binding pocket cannot be eliminated by covalent modifications.

The avidin/streptavidin-biotin system is the subject matter of several investigations due to the strong, non-covalent affinity of the binding partners ($K_A$ about $10^{15}$ l/mol). The high binding affinity has mainly been attributed to interactions between tryptophan residues of streptavidin and biotin. However, a significant decrease of the binding affinity of streptavidin variants to iminobiotin could be achieved by modifying the tryptophan residues (Chilkoti et al., Proc. Natl. Acad. Sci. USA 92 (1995) 1754–1758, Sano and Cantor, Proc. Natl. Acad. Sci. USA 92 (1995) 3180–3184). However, it was not possible to unequivocally demonstrate a reduction of the binding affinity to biotin (cf. Chilkoti et al., Supra, FIGS. 1A and 1B). Such variants are therefore unsuitable for use as interference elimination reagents since they can also specifically react with biotinylated test components due to their still very high binding affinity.

The object of the present invention was therefore to provide a reagent by means of which interfering influences on detection methods for the determination of an analyte e.g. immunoassays or nucleic acid hybridization assays can be reduced.

This object is achieved according to the invention by a polypeptide capable of binding to biotin selected from muteins of avidin and streptavidin wherein the mutein (a) differs from the native polypeptide by at least one amino acid and (b) has a binding affinity to biotin of less than $10^{10}$ l/mol.

The binding affinity for the reaction streptavidin/biotin complex⇌streptavidin+biotin is about $10^{15}$ l/mol. The streptavidin/biotin system used as a capture system is thus provided with one of the strongest known non-covalent interactions between a protein and a ligand. Surprisingly it was found that a polypeptide is obtained by substitution of one or several amino acids of streptavidin or avidin which on the one hand can be renatured when produced recombinantly and on the other hand enables the binding affinity to biotin to be reduced to <$10^{10}$ l/mol, furthermore the muteins according to the invention preferably having a structure which corresponds to the structure of the active polypeptide. The muteins according to the invention preferably have a high immunological cross-reactivity with the native polypeptide. In addition it is preferable that they are able to dimerize or tetramerize. Surprisingly the muteins like native streptavidin or avidin are able to bind to interfering sample components as they can occur in biological samples e.g. in body fluids such as serum, plasma, whole blood etc. despite the reduced binding affinity to biotin.

Due to their special properties the muteins according to the invention can be used for various applications. A lowering of the binding affinity is synonymous to lowering the interactions between biotin and the muteins. Muteins according to the invention can be designed in such a way that they under no circumstances bind to biotin or that a relatively loose reversible binding is present. Since the spatial structure of the muteins is preferably not significantly changed in comparison to the native polypeptide, interactions with other substances are not affected. A reagent is obtained in this way which corresponds in its spatial structure and its binding properties to native streptavidin or avidin with the exception of the modified binding capacity to biotin.

Aqueous samples can in general be used as test samples. In particular biological samples such as body fluids such e.g. whole blood, blood plasma, serum, saliva, tissue fluid, liquor or urine are used.

The substitution of various amino acids by mutagenesis allows a defined production of muteins. In contrast to other modifications of streptavidin such as for example chemical derivatization the structure of the muteins according to the invention is retained. Thus no interfering interactions between additionally introduced derivatization reagents and components of the sample to be tested can occur.

The binding affinity of the muteins according to the invention to biotin is preferably $<10^9$ l/mol, more preferably $<10^8$ l/mol even more preferably $<10^7$ l/mol, especially preferably $<10^6$ l/mol and most preferably $<10^5$ l/mol.

Streptavidin or avidin muteins according to the invention can preferably be regenerated when immobilized on a sensor chip surface such as a BIAcore surface.

In the case of a streptavidin mutein it is preferable to substitute one or several amino acids at positions Leu25, Ser27, Tyr43, Ser45, Val47, Gly48, Ser88, Thr90, Leu110 or/and Asp128 by another amino acid. The binding capacity of biotin can be reduced by substituting one amino acid with a small residue by an amino acid with a larger residue for example by substituting Leu or Ser by Trp, Arg, Tyr, Phe or His. In addition the binding ability of biotin can also be reduced or blocked by an additionally introduced disulfide bridge which decreases the accessibility of the biotin binding pocket. An additional disulfide bridge can for example be formed by substituting two amino acids by two cysteines at a correct spatial distance. It is also possible to reduce the biotin binding ability by additional ionic interactions. For this a positively charged amino acid such as Arg or Lys can for example be introduced which forms ionic interactions with Asp128. On the other hand it is also possible to introduce a positively charged and a negatively charged amino acid which can form a salt bridge with one another and can thus block the biotin binding pocket. Small amino acids and amino acids located at the surface such as e.g. Leu25, Ser27, Ser45 or/and Leu110 are preferably substituted by amino acids with more volume such as Arg, Trp, Tyr, Phe or His.

In order to achieve the desired binding affinity it is also possible to form muteins of streptavidin or avidin in which at least two amino acids have been substituted. In the case of streptavidin preferably at least two of the amino acids Leu25, Ser27, Ser45 and Leu110 e.g. the amino acid pairs Leu25 and Ser45, Ser27 and Ser45 or Ser45 and Leu110 are substituted by suitable amino acids especially amino acids more voluminous such as Arg, Trp, Tyr, Phe or His. It is particularly preferable to substitute Leu25 by Trp and Ser45 by Arg, Ser27 by Arg and Ser45 by Arg, Ser45 by Trp and Leu110 by Trp or Ser45 by Tyr and Leu110 by Trp.

The substitution of more than two amino acids also leads to muteins according to the invention in the case of streptavidin or avidin. In such streptavidin multiple mutants preferably at least three of the amino acids Leu25, Ser27, Ser45 and Leu110 are preferably substituted by more voluminous amino acids as defined above. In specific examples of three-fold combination mutants Leu25 was substituted by Trp, Ser45 by Trp and Leu110 by Trp or Leu25 by Trp, Ser45 by Tyr and Leu110 by Trp.

In a further preferred multiple combination mutant at least two of the amino acids Leu25, Ser27, Ser45 and Leu110 as well as additionally Trp120 are mutagenized. A specific example of such a triple mutant contains substitutions of Ser27 by Arg, Ser45 by Arg and Trp120 by Ala.

In the case of an avidin mutein one or several amino acids at positions Leu14, Ser16, Tyr33, Thr35, Val37, Thr38, Ser75, Thr77, Leu99 and Ile117 are preferably substituted. Amino acid substitutions are especially preferred at positions Leu14, Ser16, Thr35 or/and Leu99. These amino acids are preferably substituted by more voluminous amino acids such as Arg, Tyr, Trp, Phe or His. The other possibilities of substitution mentioned for streptavidin are also suitable for avidin.

The DNA sequence coding for native streptavidin is shown in SEQ ID NO.1. The respective protein sequence is shown in SEQ ID NO.2. The stated numbers of amino acids relate to this sequence. The nucleic acid sequence of native avidin is shown in SEQ ID NO.3. SEQ ID NO.4 shows the amino acid sequence of avidin. The amino acids are numbered according to this sequence.

According to the invention it is also possible to produce muteins of avidin and streptavidin variants which in their original form are capable of binding to biotin. Muteins of a shortened streptavidin (recombinant core streptavidin) are preferred according to the invention. This core streptavidin is preferably coded by the nucleotide sequence shown in SEQ ID NO. 15 and contains the amino acid sequence shown in sequence ID NO.16. The production of this core streptavidin is described in WO 93/09144. Preferred muteins of the core streptavidin contain mutations as they have already been described for native streptavidin.

A further subject matter of the present invention is a nucleic acid coding for a streptavidin or avidin mutein. This nucleic acid can for example be produced by site-specific in vitro mutagenesis of a nucleic acid according to SEQ ID NO.1, SEQ ID NO.3 or SEQ ID NO.15. The nucleic acid according to the invention can be located on a vector such as a prokaryotic plasmid preferably a plasmid which can be replicated in E. coli. The nucleic acid is located on the vector preferably in operative linkage with a promoter which allows expression in the respective host organism.

Yet a further subject matter of the invention is a cell which is transformed with a vector which contains an avidin or streptavidin mutein gene. The cell is preferably a prokaryotic cell in particular a gram-negative bacterial cell e.g. an E. coli cell.

The muteins are preferably produced by recombinant expression in a suitable host cell in particular a prokaryotic host cell such as E. coli. In this case the muteins are usually produced in the form of inactive inclusion bodies which can be renatured under suitable conditions.

The muteins can be used after renaturation and purification without further treatment in a soluble form or after immobilization on a solid phase as an interference elimination reagent. Moreover the muteins can also be used in the form of a soluble or immobilized polymer conjugate. Such polymer conjugates can be produced by chemical coupling of several mutein molecules or by coupling with other macromolecules such as polypeptides, proteins, carbohydrates etc.

Conjugates of the mutein with a further polypeptide or protein are preferred. This is especially preferably a conjugate with an albumin e.g. bovine serum albumin. The production of polymer conjugates of the muteins and optionally of further macromolecules can be carried out according to known methods (see e.g. EP-A-0 269 092).

In addition the invention concerns the use of one of the muteins described above as interference elimination reagent for assays to detect an analyte which contains the streptavidin/avidin-biotin binding pair as a test component. In this case the muteins can be used in a soluble or/and immobilized form. In one embodiment the muteins can be used together with a non-modified streptavidin/avidin solid phase in a heterogeneous assay e.g. an immunological or/and hybridization assay. In this case the muteins can be added to the test mixture in a soluble or/and immobilized form for example in the form of a separate solid phase.

The test can be carried out as a single-step or two-step process i.e. the sample to be determined can be brought into contact with the mutein and non-modified streptavidin/avidin together or in separate reaction steps.

Moreover the muteins according to the invention can also be used in other test formats e.g. in homogeneous assays, agglutination assays etc. provided that the streptavidin/avidin-biotin binding pair is present as test component. In this connection the term "biotin" encompasses biotin in its free form as well as in the form of biotinylated substances such as biotinylated nucleic acids, carbohydrates, lipids, peptides or polypeptides. In addition the term also encompasses biotin analogues and biotin derivatives such as iminobiotin, desthiobiotin and streptavidin affinity peptides.

A further subject matter of the invention is an interference elimination reagent to reduce or/and avoid unspecific interactions in a method for the determination of an analyte, wherein the interference elimination reagent contains one or several of the muteins described above. This interference elimination reagent can be present in a soluble form or/and immobilized on a solid phase preferably on a membrane, a microtitre plate, a microreagent vessel or on microbeads. Substances which interact unspecifically with assay components can be captured by the interference elimination reagent which improves the test sensitivity. The interference elimination reagent has an essentially unchanged binding capacity towards interfering components compared to non-modified avidin or streptavidin so that interfering components of the test sample are effectively captured. However, in contrast to native avidin or streptavidin the interference elimination reagent has an affinity to biotin which is practically negligible for the test which is why the detection of the analyte in the test sample is not significantly influenced.

A further subject matter of the invention is a method for the qualitative and/or quantitative detection of an analyte in a test sample comprising the use of the specific binding pair streptavidin/avidin-biotin wherein a mutein of streptavidin or avidin with a binding affinity to biotin of <$10^{10}$ l/mol is added as an interference elimination reagent.

In one embodiment of the present invention the method is a heterogeneous assay in which the analyte is determined via binding to a solid phase, the streptavidin/avidin-binding pair being involved in this solid phase binding.

In a preferred embodiment of this test format a solid phase is used which is coated with streptavidin and to which it is intended to bind a biotinylated test component. In such a test format it is possible to add the interference elimination reagent according to the invention in a soluble or/and immobilized form. An immobilized interference elimination reagent is preferably added in the form of a separate inactive solid phase, wherein the test sample is either firstly brought into contact with the inactive solid phase alone and only later with the active solid phase or simultaneously contacted with the active and inactive solid phase.

When using a soluble interference elimination reagent it is preferable to use a single-step test in which the interference elimination reagent is present in the sample liquid together with all the other test components.

The interference elimination reagent can also successfully be used when using a biotinylated solid phase and soluble streptavidin/avidin as test components e.g. in a soluble form or in the form of a separate inactive solid phase.

The analyte in the method according to the invention can be detected in a known manner by an indirect or direct label. The detection is achieved using directly labelled detection reagents in such a way that the detection reagent for example binds to the analyte and forms a detectable complex which carries the label or binds competitively to the analyte at a specific binding site. Detection reagents with indirect labelling comprises several components, the component which binds to the analyte being unlabelled and capable of binding to a further component that carries a label.

Suitable labels are known to a person skilled in the art. For example radioactive labels, chemiluminescent, fluorescent or electrochemiluminescent labels, dyed particles such as e.g. metal sol particles or dyed or undyed latex can be used. The label can also yield an indirect signal such as e.g. enzyme labels with enzymes such as peroxidase, β-galactosidase or alkaline phosphatase.

A further subject matter of the invention is a test kit to qualitatively or/and quantitatively detect an analyte in a test sample which contains a polypeptide capable of binding to biotin as well as further components of the respective assay and an interference elimination reagent which comprises a mutein according to the invention. The interference elimination reagent can be present in a soluble form or on a solid phase in particular on a microtitre plate, a microreagent vessel, a membrane or immobilized on microbeads.

A further subject matter of the invention is the use of muteins of avidin and streptavidin in which at least one amino acid of the native polypeptide is substituted and which has a binding affinity to biotin in the range of $10^5$ to $10^{11}$ l/mol as a system that can be regenerated for binding biotinylated substances. Muteins with a binding affinity to biotin in the range of $10^5$ to $10^{10}$ l/mol and in particular $10^5$ to $10^8$ l/mol are preferred.

The system that can be regenerated for binding biotinylated substances preferably comprises a solid phase on which the streptavidin muteins are immobilized. Examples of suitable solid phases are sensor chips (e.g. the Biacore system of the Kabi Pharmacia Co), reaction vessels such as polystyrene tubes or cuvettes, microtitre plates, microbeads, latex particles and support materials for affinity columns. The term "biotinylated substances" is in particular to be understood as conjugates of biotin and biotin analogues, biotin analogues being those substances which form a complex with the biotin binding pocket of (native) streptavidin or avidin such as iminobiotin, desthiobiotin and streptavidin affinity peptides.

The advantage of the solid phases that can be regenerated according to the invention in comparison to a solid phase coated with native streptavidin/avidin is that they have on the one hand an adequately high binding affinity for biotin (in the form of free biotin or biotinylated substances) so that the solid phase can be used in assays for the detection of analytes, for the investigation of receptor-ligand interactions and for the purification or analysis of biotinylated substances. On the other hand the binding affinity of the solid phase to biotin or a biotinylated substance is sufficiently low to enable a regeneration of the solid phase i.e. it is possible to detach the biotin. This detachment is preferably carried out by reducing the pH value to pH <4.5 or/and by addition of chaotropic substances i.e. substances which interfere with the formation of hydrogen bridges. Alternatively the detachment for isolating the biotinylated substances can also be achieved by adding free biotin or/and biotin analogues. Gradient elution is particularly preferred.

In a preferred embodiment the solid phase capable of regeneration can be used as an affinity matrix. This affinity matrix is used to purify biotinylated substances such as biotinylated antibodies or to separate such substances based on the number of biotin residues bound per molecule. If non-modified streptavidin or avidin is used as the matrix, it is practically impossible to release the substances brought into contact with the matrix due to the high binding affinity. Attempts have been made in the state of the art to solve this problem by converting avidin into its monomers by treatment with urea or by using iminobiotin instead of biotin in order to lower the binding affinity. However, these methods are time-consuming and associated with additional problems. Using muteins according to the invention it is possible to produce affinity matrices with binding affinities to biotin which enable a reversible binding and thus recovery of the analyte.

In addition it is preferred to use the solid phase that can be regenerated according to the invention to determine receptor/ligand interactions e.g. as a coated sensor chip. The binding of molecules to this surface can for example be examined by surface plasmon resonance spectroscopy.

The plasmids and microorganisms mentioned in the present application have been deposited under the following deposit numbers at the "Deutsche Sammlung von Mikroorganismen und Zellkulturen GmbH" (DSM), Mascheroderweg 1B, D-30300 Braunschweig according to the rules of the Budapest treaty.

| E. coli K12RM82 | DSM 5445 on 2nd October 1991 |
| pUBS500 | DSM 6720 on 20th September 1991 |

In the sequence list

SEQ ID NO.1 shows the nucleotide sequence coding for streptavidin including the sequence coding for the signal peptide SEQ ID NO.2 shows the amino acid sequence of streptavidin including the signal sequence SEQ ID NO.3 shows the nucleotide sequence coding for avidin including the sequence coding for the signal peptide SEQ ID NO.4 shows the protein sequence of avidin including the signal sequence SEQ ID NO.5 shows the nucleotide sequence of primer N1, SEQ ID NO.6 shows the nucleotide sequence of primer N2, SEQ ID NO.7 shows the nucleotide sequence of primer N3, SEQ ID NO.8 shows the nucleotide sequence of primer N4, SEQ ID NO.9 shows the nucleotide sequence of primer N5, SEQ ID NO.10 shows the nucleotide sequence of primer N6, SEQ ID NO.11 shows the nucleotide sequence of primer N7, SEQ ID NO.12 shows the nucleotide sequence of primer N8, SEQ ID NO.13 shows the nucleotide sequence of primer N9, SEQ ID NO.14 shows the nucleotide sequence of primer N10, SEQ ID NO.15 shows the nucleotide sequence coding for core streptavidin according to WO 93/09144 and SEQ ID NO.16 shows the amino acid sequence of core streptavidin.

FIG. 1 shows the plasmid map of the core streptavidin expression plasmid pSAM core.

The invention is elucidated in more detail by the following examples.

Example 1

Construction of Core Streptavidin Mutant Genes

The plasmid pSAM-core was prepared according to WO 93/09144.

The DNA region upstream and downstream of the mutation to be introduced was removed up to the next singular restriction endonuclease cleavage site in the pSAM-core expression vector and replaced by a corresponding chemically produced DNA segment having the desired mutation (DNA adaptor). The manipulation of the DNA was in this case carried out with standard methods as described in Sambrook et al., In: Molecular Cloning. A Laboratory Manual, Cold Spring Harbor Laboratory Press, Cold Spring Harbor, N.Y., 1989. The molecular biological reagents used were used according to the instructions of the manufacturer.

The protein concentrations of the fusion proteins and peptides were determined based on the optical density (OD) at 280 nm using molar extinction coefficients (e.g. for core-SA: $\epsilon=41820$ $cm^2/mol$) calculated by means of the amino acid sequences.

Construction of Streptavidin Mutants

Single mutants:

1.1 pSA-Leu25Trp:

For the construction of the Leu25Trp CORE-SA mutant gene the plasmid PSAM-CORE was digested with singular cleaving restriction endonucleases NcoI and SalI and after isolation the ca. 2.9 kbp long NcoI/SalI-pSAM-CORE vector fragment was ligated with the Leu25Trp adaptor by agarose gel electrophoresis. The Leu25Trp adaptor was prepared by hybridization from the complementary oligonucleotides N1 and N2 (reaction buffer: 12.5 mmol/l Tris-HCl, pH 7.0 and 12.5 mmol/l $MgCl_2$; N-concentration: 1 pmol/60 µl in each case). N1 and N2 were both designed such that after hybridization the NcoI and SalI overhangs form that are relevant for the cloning.

The newly formed plasmid pSA-Leu25Trp was examined by restriction mapping (deletion of the BanI restriction endonuclease cleavage site by silent mutation in the Leu25Trp adaptor) and the DNA sequence of the adaptor region was examined by DNA sequencing.

Leu25Trp adaptor:

```
N1: 5'-CATGGCCGAAGCTGGTATCACTGGGACCTGGTATAACCAATGGGGG-3'
N2: 5'-TCGACCCCCATTGGTTATACCAGGTCCCAGTGATACCAGCTTCGGC-3'

NcoI overhang   dele.BanI              Trp instead of Leu
5'-CATGGCCGAAGCTGGTATCACTGGGACCTGGTATAACCAATGGGGG-3'
3'-    CGGCTTCGACCATAGTGACCCTGGACCATATTGGTTACCCCAGCT-5'
                                                SalI overhang
```

1.2 pSA-Ser27Arg:

For the construction of the Ser27Arg CORE-SA mutant gene the plasmid pSAM-CORE was digested with the singularly cleaving restriction endonucleases NcoI and HindIII and the ca. 400 bp long streptavidin fragment and the ca. 2.5 kbp pSAM-CORE vector fragment were isolated by means of agarose gel electrophoresis. The desired mutation Ser27Arg was introduced by means of PCR technology by amplification of the 400 bp long fragment containing the 5'-mutagenesis primer N3 that had been designed accordingly. The PCR product isolated in this way was afterwards recleaved with NcoI and HindIII, purified by means of agarose gel electrophoresis and ligated with the 2.5 kbp pSAM-CORE vector fragment that was isolated as described above.

The newly formed plasmid pSA-Ser27Arg was examined by restriction mapping (deletion of the SalI restriction endonuclease cleavage site by introduction of the mutation Ser27Arg) and the mutated DNA sequence of the 5' region was examined by DNA sequencing.

Ser27Arg:

PCR was carried out using the 5' mutagenesis primer N3 (has the desired Ser27Arg mutation) and the 3' streptavidin primer N4 (sequence unchanged compared to pSAM-CORE).

```
             SacI       AvaII     Arg instead of Ser
N5: 5'-GACGGAGCTCTGACTGGGACCTACGAAGGGGCGGTTGGTA-3'

HindIII
N4: 5'-CGCGAAGCTTCAGCTGTCATTAGCTA-3'
```

1.4 pSA-Trp120Ala

For the construction of the Trp120Ala CORE-SA mutant gene the plasmid PSAM-CORE was digested with the singularly cleaving restriction endonucleases NsiI and SpeI and the ca. 2.9 kbp long NsiI/SpeI-pSAM-CORE vector fragment was ligated with the Trp120Ala adaptor after isolation by means of agarose gel electrophoresis. The Trp120Ala adaptor was produced by hybridization from complementary oligonucleotides N9 and N10 (reaction buffer: 12.5 mmol/l Tris-HCl, pH 7.0 and 12.5 mmol/l MgCl$_2$; N-concentration: 1 pmol/60 μl in each case). N9 and N10 were in each case designed in such a way that the NsiI and SpeI overhangs relevant for the cloning form after hybridization.

The newly formed plasmid pSA-Trp120Ala was examined by restriction mapping (deletion of the NsiI restriction endonuclease cleavage site by desired mutation in the

```
            NcoI                        Arg instead of Ser
N3: 5'-GCGCCATGGCCGAAGCTGGTATCACTGGCACCTGGTATAACCAACTGGGGCGGACTTTC-3'

HindIII
N4: 5'-CGCGAAGCTTCAGCTGTCATTAGCTA-3'
```

1.3. pSA-Ser45Arg:

For the construction of the Ser45Arg CORE-SA mutant gene the plasmid PSAM-CORE was digested with singularly cleaving restriction endonucleases SacI and HindIII and the ca. 300 bp long streptavidin fragment and the ca. 2.6 kbp pSAM-CORE vector fragment was isolated by means of agarose gel electrophoresis. The desired mutation Ser4sArg was introduced by means of PCR technology by amplification of the ca. 300 bp long fragment containing the 5' mutagenesis primer N5 that had been designed accordingly. The PCR product obtained in this way was afterwards recleaved with SacI and HindIII, purified by means of agarose gel electrophoresis and ligated with the 2.6 kbp PSAM-CORE vector fragment that had been isolated as described above.

The newly formed plasmid pSA-Ser45Arg was examined by restriction mapping (additional AvaII restriction endonuclease cleavage site by silent mutation in the N5 mutagenesis primer) and the mutated DNA sequence of the 5' region was examined by DNA sequencing.

Ser45Arg:

The PCR was carried out using the 5' mutagenesis primer N5 (has the desired Ser45Arg mutation) and the 3' strepta- Trp120Ala adaptor) and the DNA sequence of the adaptor region was examined by means of DNA sequencing.

Trp12Ala-Adaptor:

```
N9:  5'-GCGAAATCGACA-3'
N10: 5'-ACTAGTGTCG ATTTCGCTGC AT-3'

NsiI overhang       Ala          SpeI overhang

N9:            GCGAAATCGACA
N10:      TACGTCGCTTTAGCTGTGATCA
```

Double combination mutants:

1.5 pSA-Leu25Trp/Ser45Arg:

For the construction of the Leu25Trp/Ser45Arg CORE-SA mutant gene the plasmids pSA-Leu25Trp and pSA-Ser45Arg were digested with the singularly cleaving restriction endonucleases NcoI and SacI and the 82 bp long fragment of pSA-Leu25Trp and the ca. 2.8 kbp long vector fragment of pSA-Ser45Arg were isolated by means of agarose gel electrophoresis. Subsequently both fragments were ligated together.

The newly formed plasmid pSA-Leu25Trp/Ser45Arg was examined by restriction mapping (missing BanI restriction endonuclease cleavage site from pSA-Leu25Trp and additional AvaII restriction endonuclease cleavage site from pSA-Ser45Arg) and the DNA sequence in the 5' region was examined by means of DNA sequencing.

endonuclease cleavage site) and the 3' mutagenesis primer N7 (it has the desired mutation Lue110Trp and the NsiI restriction endonuclease cleavage site).

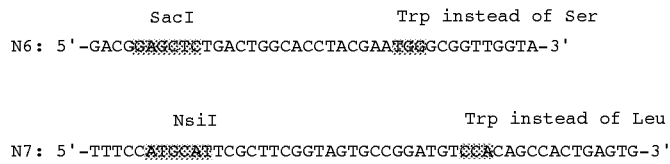

1.6 PSA-Ser27Arg/Ser45Arg:

For the construction of the Ser27Arg/Ser45Arg CORE-SA mutant gene the plasmids pSA-Ser27Arg and pSA-Ser45Arg were digested with the singularly cleaving restriction endonucleases NcoI and SacI and the 82 bp long fragment of pSA-Ser27Arg and the ca. 2.8 kbp long vector fragment of pSA-Ser45Arg were isolated by means of agarose gel electrophoresis. Subsequently both fragments were ligated with one another.

The newly formed plasmid pSA-Ser27Arg/Ser45Arg was examined by restriction mapping (missing SalI restriction endonuclease cleavage site from pSA-Ser27Arg and additional AvaII restriction endonuclease cleavage site from pSA-Ser45Arg) and the DNA sequence in the 5' region was examined by means of DNA sequencing.

1.7. pSA-Ser45Trp/Leu110Trp:

For the construction of the Ser45Trp/Leu110Trp CORE-SA mutant gene the plasmid pSA-Ser45Arg was digested with the singularly cleaving restriction endonucleases SacI and NsiI and the 243 bp long streptavidin fragment and the ca. 2.7 kbp long pSA-Ser45Arg vector fragment was isolated by means of agarose gel electrophoresis. The desired mutations Ser45Trp/Leu110Trp were subsequently introduced by means of PCR technology by amplification of the 243 bp long fragment with the respectively designed 5' mutagenesis primer N6 and the respectively designed 3' mutagenesis primer N7. The PCR product isolated in this way was afterwards recleaved with SacI and NsiI, purified by means of agarose gel electrophoresis and ligated with the ca. 2.7 kbp pSA-Ser45Arg vector fragment isolated as described above.

The newly formed plasmid was examined by restriction mapping (deletion of the AvaII cleavage site additionally introduced by silent mutation into pSA-Ser45Arg by back-mutation into the original sequence as well as deletion of the HindIII site by the Leu110Trp mutation) and the desired DNA mutations were examined by DNA sequencing.

Ser45Trp/Lue110Trp:

PCR was carried out using the 5' mutagenesis primer N6 (it has the desired mutation Ser45Trp and the SacI restriction

1.8. pSA-Ser45Tyr/Lue110Trp:

For the construction of the Ser45Tyr/Lue110Trp CORE-SA mutant gene the plasmid pSA-Ser45Arg was digested with the singularly cleaving restriction endonucleases SacI and NsiI and the 243 bp long streptavidin fragment and the ca. 2.7 kbp long pSA-Ser45Arg vector fragment were isolated by means of agarose gel electrophoresis. The desired mutations Ser45Tyr/Lue110Trp were subsequently introduced by means of PCR technology by amplification of the 243 bp long fragment using the respectively designed 5' mutagenesis primer N8 and the respectively designed 3' mutagenesis primer N7. The PCR product obtained in this way was afterwards recleaved with SacI and NsiI, purified by means of agarose gel electrophoresis and ligated with the ca. 2.7 kbp pSA-Ser45Arg vector fragment isolated as described above.

The newly formed plasmid was examined by restriction mapping (deletion of the AvaII cleavage site additionally introduced by silent mutation into pSA-Ser45Arg by back-mutation into the original sequence as well as deletion of the HindII site by the Lue110Trp mutation) and the desired DNA mutations were examined by DNA sequencing.

Ser45Tyr/Lue110Trp:

PCR was carried out using the 5' mutagenesis primer N8 (it has the desired mutation Ser45Tyr and the SacI restriction endonuclease cleavage site) and the 3' mutagenesis primer N7 (it has the desired mutation Lue110Trp and the NsiI restriction endonuclease cleavage site).

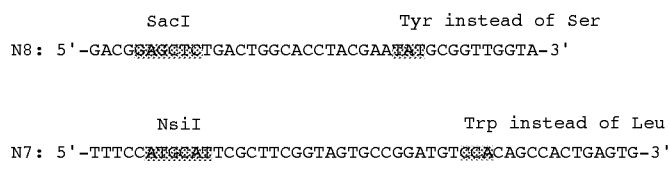

Triple combination mutations:

1.9 pSA-Leu25Trp/Ser45Trp/Lue110Trp:

For the construction of the Leu25Trp/Ser45Trp/Lue110Trp CORE-SA mutant gene the plasmids pSA-Leu25Trp and pSA-Ser45Trp/Lue110Trp were digested with the singularly cleaving restriction endonucleases SalI and HindIII and the 352 bp long fragment of pSA-Ser45Trp/Lue110Trp and the ca. 2.6 kbp long vector fragment of pSA-Leu25Trp were isolated by means of agarose gel electrophoresis. Subsequently both fragments were ligated with one another.

The newly formed plasmid pSA-Leu25Trp/Ser45Trp/Leu110Trp was examined by means of restriction mapping (missing HindII restriction endonuclease cleavage site from pSA-Ser45Trp/Lue110Trp and missing BanI restriction endonuclease cleavage site from pSA-Leu25Trp) and examined by means of DNA sequencing.

1.10 pSA-Leu25Trp/Ser45Tyr/Leu110Trp:

For the construction of the Leu25Trp/Ser45Tyr/Lue110Trp CORE-SA mutant gene the plasmids pSA-Leu25Trp and pSA-Ser45Tyr/Lue110Trp were digested with the singularly cleaving restriction endonucleases SalI and HindIII and the 352 bp long fragment of pSA-Ser45Tyr/Lue110Trp and the ca. 2.6 kbp long vector fragment of pSA-Leu25Trp were isolated by means of agarose gel electrophoresis. Subsequently both fragments were ligated with one another.

The newly formed plasmid pSA-Leu25Trp/Ser45Trp/Leu110Trp was examined by means of restriction mapping (missing HindII restriction endonuclease cleavage site from pSA-Ser45Trp/Lue110Trp and missing BanI restriction endonuclease cleavage site from pSA-Leu25Trp) and the DNA sequence was examined by means of DNA sequencing.

1.11 pSA-Ser27Arg/Ser45Arg/Lue110Trp:

For the construction of the Ser27Arg/Ser45Arg/Lue110Trp CORE-SA mutant gene the plasmids pSA-Ser27Arg/Ser45Arg and pSA-Ser45Trp/Lue110Trp were digested with the singularly cleaving restriction endonucleases KpnI and HindIII and the 218 bp long fragment of pSA-Ser45Trp/Leu100Trp and the ca. 2.7 kbp long vector fragment of pSA-Ser27Arg/Ser45Arg were isolated by means of agarose gel electrophoresis. Subsequently both fragments were ligated with one another.

The newly formed plasmid pSA-Ser27Arg/Ser45Arg/Leu110Trp was examined by means of restriction mapping (missing HindII restriction endonuclease cleavage site from pSA-Ser27Arg/Ser45Arg and pSA-Ser45Trp/Lue110Trp and an additional AvaII restriction endonuclease cleavage site from pSA-Ser27Arg/Ser45Arg) and the DNA sequence was examined by means of DNA sequencing.

1.12 pSA-Ser27Arg/Ser45Arg/Trp120Ala

For the construction of the Ser27Arg/Ser45Arg/Trp120Ala CORE-SA mutant gene the plasmid pSA-Ser27Arg/Ser45Arg was digested with the singularly cleaving restriction endonucleases NsiI and SpeI and the ca. 2.9 kbp long NsiI/SpeI-pSAM-CORE vector fragment was ligated with the Trp120Ala adaptor after isolation by means of agarose gel electrophoresis. The Trp120Ala adaptor was produced by hybridization from the complementary oligonucleotides N9 and N10 (reaction buffer: 12.5 mmol/l Tris-HCl, pH 7.0 and 12.5 mmol/l MgCl$_2$; N-concentration: 1 pmol/60 μl each time). N9 and N10 were each designed in such a way that NsiI and SpeI overhangs relevant for cloning form after hybridization.

The newly formed plasmid pSA-Ser27Arg/Ser45Arg/Trp120Ala was examined by restriction mapping (deletion of the NsiI restriction endonuclease cleavage site by desired mutation in the Trp120Ala adaptor) and the DNA sequence of the adaptor region was examined by means of DNA sequencing.

EXAMPLE 2

Characterization of Purified Inactive Core Streptavidin Muteins from *E. coli*

2.1 Expression

The expression of the core streptavidin muteins in *E. coli*, the expression analysis, the preparation and the purification of renatured inactive core streptavidin muteins was carried out as described in EP-A-0 612 325 for recombinant core streptavidin. An S-Sepharose equilibrated in 20 mM Na-acetate, pH 5.0 was used instead of Q-Sepharose for the purification of the double mutant SA-Ser27Arg/Ser45Arg and the triple mutant SA-Ser27Arg/Ser45Arg/Lue110Trp. They were eluted in 20 mM Na-acetate, pH 5.0 containing 350 mM NaCl.

In comparison to the other mutants the SA mutant Trp120Ala has a reduced acid stability which indicates an incorrect structural folding and disturbances of the protein backbone.

2.2 SDS-PAGE/isoelectric focussing (IF)

The homogeneity and purity of the renatured purified inactive core streptavidin muteins was examined by means of SDS-PAGE (Laemmli, Nature 227 (1970) 680–685) and isoelectric focussing (Bark et al., J. Forensic Sci. Soc. 16 (1976) 115–120).

The renatured purified inactive core streptavidin muteins were homogeneous (single-band) in the SDS-PAGE (molecular weight ca. 13500 Da) and had a purity of >98% in the IF gels.

EXAMPLE 3

Determination of the Affinity of Recombinant Streptavidin Mutants

The affinity of the streptavidin muteins to biotin derivatives (constants $K_{on}$, $K_{off}$ and $K_A$) was determined in comparison to core streptavidin (wild type streptavidin) using the BIAcore system from the Pharmacia Co. For this the respective streptavidin samples were immobilized on the surface of biosensor chips (CM5 biosensor). The surface loading was selected in such a way that a measurement signal of 500 to 2000 resonance units (rU) was generated. The association kinetics were recorded for 3 min in each case at 25° C. and with 6 concentrations (12.5, 25, 50, 100, 200 and 400 nmol/l ) of a monobiotinylated Fab' antibody fragment. In order to investigate the influence of the reverse binding of the antibody, the dissociation kinetics in the absence and presence of 10 μg/ml core streptavidin were compared. The specificity of the binding was shown by an experiment with the same body in a non-biotinylated form (negative control).

The binding constants were determined for the purified streptavidin muteins as well as for streptavidin muteins cross-linked with a polymer (streptavidin-mutein thermobovine serum albumin conjugates, preparation: EP-A-0 092). The results of the experiment are shown in Table 1.

TABLE 1

| Streptavidin wild-type mutein | $K_{on}$ 1/mol.s | $K_{off}$ 1/s | $K_A$ 1/mol | t/2 diss min | Regenerability |
|---|---|---|---|---|---|
| wild-type | $2.2 \cdot 10^5$ | $<10^{-5}$ | $>10^{10}$ | >20h | no |
| SA-Ser27Arg/Ser45Arg (1) | $1.3 \cdot 10^5$ | $3.1 \cdot 10^3$ | $4.2 \cdot 10^7$ | 3.7 | yes |
|  | $8.5 \cdot 10^4$ | $4.1 \cdot 10^{-3}$ | $2.1 \cdot 10^7$ | 2.8 |  |
| SA-Ser45Trp/Leu110Trp | $1.4 \cdot 10^5$ | $3.3 \cdot 10^{-4}$ | $6.1 \cdot 10^8$ | 40.8 | yes |
| SA-Ser45Tyr/Leu110Trp | $1.3 \cdot 10^5$ | $5.4 \cdot 10^{-4}$ | $2.7 \cdot 10^8$ | 22.6 | yes |
| SA-Leu25Trp/Ser45Arg | $7.9 \cdot 10^4$ | $2.2 \cdot 10^{-4}$ | $3.6 \cdot 10^8$ | 51.8 | yes |
| SA-Ser27Arg/Ser45Arg TBSA conjugate | $1.0 \cdot 10^5$ | $3.0 \cdot 10^{-3}$ | $3.3 \cdot 10^7$ | 3.9 | yes |
| SA-Leu25Trp/Ser45Trp/Leu110Trp | $4.9 \cdot 10^4$ | $8.7 \cdot 10^{-4}$ | $7.0 \cdot 10^7$ | 13.4 | yes |

TABLE 1-continued

| Streptavidin wild-type mutein | $K_{on}$ 1/mol.s | $K_{off}$ 1/s | $K_A$ 1/mol | t/2 diss min | Regenerability |
|---|---|---|---|---|---|
| SA-Leu25Trp/ Ser45Tyr/ Leu110Trp | $5.4 \cdot 10^4$ | $1.3 \cdot 10^{-3}$ | $4.6 \cdot 10^7$ | 8.7 | yes |
| SA-Ser27Arg/ Ser45Arg/ Leu110Trp | $4.5 \cdot 10^4$ | $5.9 \cdot 10^{-3}$ | $7.7 \cdot 10^6$ | 2.0 | yes |
| SA-Trp120Ala | $6.7 \cdot 10^4$ | $2.3 \cdot 10^{-4}$ | $2.9 \cdot 10^8$ | 49.4 | yes |
| SA-Ser27Arg/ Ser45ARg/ Trp120/Ala | $1.0 \cdot 10^5$ | $5.2 \cdot 10^{-3}$ | $2.0 \cdot 10^7$ | 2.2 | yes |

(1) data from 2 product lots

EXAMPLE 4

Interference Elimination Experiment

An enzyme immunoassay for anti-HCV antibodies was carried out and the reduction of test interferences by addition of the streptavidin muteins SA-Ser27Arg/Ser45Arg (1), SA-Ser45Trp/Lue110Trp (2) and SA-Ser45Tyr/Lue110Trp (3) was determined.

The test was carried out as a two-step sandwich assay using a streptavidin solid phase. In the first step biotinylated HCV peptides (EP-A-0 582 243, EP-A-0 484 787) or polypeptides (EP-A-0 696 640) plus sample were added. In the second step a reaction of the solid phase-bound antibody with an anti-human-IgG-peroxidase conjugate was carried out. Subsequently an indicator reaction was carried out using ABTS as the substrate.

The test was carried out as follows:

Incubation buffer 40 mmol/l Na phosphate pH: 7.4
7.1 g/l NaCl
   preservative (e.g. chloroacetamide)

200 g/l Plasma-Diagnostic Base
   (Armour Pharmaceuticals Company, USA) +
   HCV peptides from the core, NS4 and
   NS3 region and recombinant NS3 polypeptide
   (biotinylated) ±
 25 μg/ml streptavidin mutein unconjugated or
 75 μg/ml as conjugate with thermo-BSA ±
 25 μg/ml core streptavidin (WT)
     Conjugate buffer 40 mmol/l Na phosphate pH: 7.4
 7.1 g/l NaCl
     preservative (e.g. chloroacetamide)
  1 g/l bovine serum albumin
  4 g/l bovine IgG
  1 g/l Triton X 100
 15 U/l anti-human IgG POD
     Incubation periods Step 1: 1 hour (sample + incubation buffer)
Step 2: 1 hour (+ conjugate buffer)
Step 3: 1 hour (substrate reaction with ABTS)
   Test was carried out on ES 600 at 25° C.
   Substrate solution was measured at 422 nm
       Samples 5 false-positive anti-HCV-negative samples
   (interfering samples)
 6 positive anti-HCV sanples (control)
       Volumes 20 μl sample, all other reagents 500 μl in each case The absorbance values measured on the ES 600 analyzer at 422 nm are shown in the following tables 2 and 3. The results show that the addition of streptavidin muteins results in a very strong decrease of the signal for negative serum samples but no or only a very slight signal decrease for the positive serum samples. The streptavidin mutein is thus excellently suitable as interference elimination reagent.

TABLE 2

| Samples | without addition in the buffer | with SA mutein (1) in the buffer | with SA mutein (1) conjugate in the buffer | with core-SA (wt) in the buffer | % signal decrease after addition SA mutein | SA mutein conugate |
|---|---|---|---|---|---|---|
| HCV negative serum 1 | 0.324 | 0.174 | 0.175 | 0.002 | 46% | 46% |
| HCV negative serum 2 | 0.838 | 0.221 | 0.109 | 0.652 | 74% | 87% |
| HCV negative serum 3 | 1.675 | 1.025 | 0.538 | 0.256 | 39% | 68% |
| HCV negative serum 4 | 2.854 | 1.413 | 1.283 | 0.660 | 50% | 55% |
| HCV negative serum 5 | 4.935 | 2.661 | 2.511 | 1.403 | 46% | 49% |
| HCV positive serum 1 | 5.152 | 5.219 | 4.722 | 0.061 | −1% | 8% |
| HCV positive serum 2 | 1.051 | 1.235 | 0.896 | 0.023 | −18% | 15% |
| HCV positive serum 3 | 2.730 | 2.585 | 2.385 | 0.027 | 5% | 13% |
| HCV positive serum 4 | 5.030 | 5.111 | 4.629 | 0.008 | −2% | 8% |
| HCV positive serum 5 | 2.244 | 2.216 | 1.782 | 0.003 | 1% | 21% |
| HCV positive serum 6 | 4.920 | 4.612 | 4.523 | 0.006 | 6% | 8% |

TABLE 3

| Samples | without addition in the buffer | mutein (2) in the buffer | mutein (3) in the buffer | with core-SA (wt) in the buffer | % signal decrease after additon of SA mutein | |
|---|---|---|---|---|---|---|
| | | | | | (2) | (3) |
| HCV negative serum 1 | 0.221 | 0.105 | 0.052 | 0.452 | 52% | 76% |
| HCV negative serum 2 | 1.002 | 0.238 | 0.248 | 0.652 | 76% | 75% |
| HCV negative serum 3 | 2.195 | 1.003 | 1.118 | 0.494 | 54% | 49% |
| HCV negative serum 4 | 3.143 | 1.606 | 1.643 | 0.660 | 49% | 48% |
| HCV negative serum 5 | 6.419 | 2.961 | 3.222 | 2.518 | 54% | 50% |
| HCV positive serum 1 | 5.349 | 5.604 | 5.199 | 0.016 | −5% | 3% |
| HCV positive serum 2 | 0.949 | 1.050 | 0.954 | 0.012 | −11% | −1% |
| HCV positive serum 3 | 2.862 | 2.619 | 2.664 | 0.003 | 8% | 7% |
| HCV positive serum 4 | 0.549 | 0.516 | 0.515 | 0.015 | 6% | 6% |
| HCV positive serum 5 | 4.287 | 4.089 | 4.727 | 0.003 | 5% | −10% |

EXAMPLE 5

Use of Streptavidin Muteins as Affinity Adsorbents 5.1 Immobilizing SA mutein on Spherosil-NH$_2$ Spherosil-NH2 (Boehringer Mannheim, Order Number: 576590) was activated using a three-fold amount of 10% (w/v) glutardialdehyde and then washed with 7 volumes distilled water. The streptavidin mutein was coupled to the free aldehyde groups that form via its free amino groups. The SA mutein concentration used was 2 mg streptavidin mutein per ml activated Spherosil-NH$_2$ gel. The mutein not bound to Spherosil was washed out with PBS buffer (50 mM K-phosphate, pH 7.5, 150 MM NaCl).

Subsequently the adsorbent was loaded with biotinylated substances. Non-biotinylated substances were not bound and could thus be easily separated from the biotinylated substances. It was also possible to separate biotinylated substances according to their degree of biotinylation (number of biotin groups per molecule).

It was possible to elute the biotinylated substances bound to the column using a buffer of pH<4.5 or/and by adding chaotropic substances such as e.g. guanidinium hydrochloride or/and by adding biotin or biotin analogues. The biotinylated substances were preferably separated according to their degree of biotinylation by means of a biotin or biotin analogue gradient.

5.2 Immobilization of SA mutein to other supports

Immobilization of streptavidin muteins on other chromatography materials can be achieved by all known methods for native streptavidin.

5.3 Loading an SA mutein adsorber with biotinylated bovine serum albumin (Bi-BBA)

The Spherosil-NH$_2$ SA mutein adsorber produced in example 5.1 was equilibrated in PBS buffer (50 mM K-phosphate, pH 7.5, 150 mM NaCl) and transferred to a chromatography column. 2 mg Bi-BSA in PBS were then applied per ml SA mutein adsorber. Unbound protein was washed out with 2 column volumes PBS. It was eluted in 50 mM ammonium acetate, pH 3.0 or/and a gradient of 9 to 10 mM iminobiotin or biotin.

5.4 Loading an SA mutein adsorber with a biotinylated Fab antibody fragment

The SA mutein adsorber produced in example 5.1 was equilibrated in PBS buffer containing 500 mM ammonium sulfate (PBS+AS buffer) and transferred to a chromatography column. 2 mg antibody fragment per ml SA mutein adsorber in PBS+AS buffer was then applied. Unbound protein was washed out with 2 column volumes PB+AS buffer. It was eluted with PBS buffer, pH 7.2 and a gradient of 0 to 10 mM biotin.

What is claimed is:

1. An isolated polypeptide which is capable of binding to biotin and has an affinity therefore of less than $10^{10}$ l/mol, which is a mutein of avidin which differs in its amino acid sequence by at least one amino acid as compared to avidin.

2. The polypeptide of claim 1, wherein said mutein of avidin differs from avidin in at least two amino acids.

3. The polypeptide of claim 1, wherein said mutein of avidin differs from avidin in that at least 3 amino acids are substituted.

4. An isolated polypeptide which is a mutein of avidin which has the amino acid sequence set out at SEQ ID NO: 3, wherein said mutein has an amino acid sequence which differs from the amino acid sequence of avidin set forth in SEQ ID NO: 3 by having a different amino acid at at least one position selected from the group consisting of Leu 14, Ser 16, Tyr 33, Thr 35, Val 37, Thr 38, Ser 75, Thr 77, Leu 99, and Ile 117, and which is capable of binding to biotin with an affinity less than $10^{10}$ l/mol.

5. The polypeptide of claim 4, wherein said mutein has a different amino acid at at least one position selected from the group consisting of Leu 14, Ser 16, Thr 35, and Leu 99.

6. The polypeptide of claim 5, wherein said at least one position is replaced by Arg, Trp, Tyr, Phe, or His.

7. The polypeptide of claim 4, wherein said mutein differs from avidin in at least two amino acid positions.

8. The polypeptide of claim 7, wherein said at least two amino acid positions are substituted by Arg, Trp, Tyr, Phe or His.

9. The polypeptide of claim 2, wherein said mutein of avidin differs from avidin as set forth in SEQ ID NO: 3 in at least two positions, selected from the group consisting of Leu 14, Ser 16, Thr 35 and Leu 99.

10. The polypeptide of claim 9, wherein said at least two positions are substituted by Arg, Trp, Tyr, Phe or His.

11. The polypeptide of claim 3, wherein said mutein of avidin differs from avidin as set forth in SEQ ID NO: 3 in at least three positions, selected from the group consisting of Leu 14, Ser 16, Thr 35 and Leu 99.

12. The polypeptide of claim 11, wherein said positions are substituted by Arg, Trp, Tyr, Phe or His.

13. A polymeric conjugate comprising the polypeptide of claim 1 and a second molecule conjugated thereto.

14. A polymeric conjugate comprising the polypeptide of claim 4 and a second molecule conjugated thereto.

15. A polymeric conjugate comprising the polypeptide of claim 11 and a second molecule conjugate thereto.

16. The polymeric conjugate of claim 13, 14 or 15, wherein said second molecule is a polypeptide or a protein.

17. The polymeric conjugate of claim 16, wherein said second molecule is bovine serum albumin.

18. The polypeptide of claim 1 or 4 wherein said polypeptide is capable of forming a dimer or a tetramer.

19. The polypeptide of claim 11, wherein said polypeptide is capable of forming a dimer or a tetramer.

20. Interference elimination reagent comprising the polypeptide of claim 1, 4, or 11 immobilized to a solid phase.

21. The interference elimination reagent of claim 20, wherein said solid phase is a chip, a membrane, a microtitre plate, a reaction vessel, or a microbead.

22. A method for determining an analyte in a sample, comprising adding an analyte detection system to said sample, said sample comprising biotin and avidin, and the polypeptide of claim 1, 4, or 11 in an amount sufficient to reduce any interference with binding of said biotin and avidin and determining said analyte.

23. Composition comprising an isolated mutein of avidin which has affinity for biotin of from about $10^5$ to about $10^{11}$ l/mol, wherein said mutein differs from avidin by at least one amino acid, coated onto a solid phase.

24. The polypeptide of claim 1, wherein said mutein of avidin differs from avidin in that amino acids Leu 14, Ser 16, Thr 35 and Leu 99 are substituted.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 638 base pairs
      (B) TYPE: nucleic acid
      (C) STRANDEDNESS: single
      (D) TOPOLOGY: linear (ix) FEATURE:
      (A) NAME/KEY: CDS
      (B) LOCATION:50..598
      (D) OTHER INFORMATION:Positions 50..121 correspond
         to sig peptide, and 122..598 to mat peptide.

(xi) SEQUENCE DESCRIPTION: SEQ ID NO: 1:

```
CCCTCCGTCC CCGCCGGGCA ACAACTAGGG AGTATTTTTC GTGTCTCAC ATG CGC           55
                                                      Met Arg
                                                      -24

AAG ATC GTC GTT GCA GCC ATC GCC GTT TCC CTG ACC ACG GTC TCG ATT       103
Lys Ile Val Val Ala Ala Ile Ala Val Ser Leu Thr Thr Val Ser Ile
        -20             -15             -10

ACG GCC AGC GCT TCG GCA GAC CCC TCC AAG GAC TCG AAG GCC CAG GTC       151
Thr Ala Ser Ala Ser Ala Asp Pro Ser Lys Asp Ser Lys Ala Gln Val
        -5              1               5                   10

TCG GCC GCC GAG GCC GGC ATC ACC GGC ACC TGG TAC AAC CAG CTC GGC       199
Ser Ala Ala Glu Ala Gly Ile Thr Gly Thr Trp Tyr Asn Gln Leu Gly
            15              20                  25

TCG ACC TTC ATC GTG ACC GCG GGC GCC GAC GGC GCC CTG ACC GGA ACC       247
Ser Thr Phe Ile Val Thr Ala Gly Ala Asp Gly Ala Leu Thr Gly Thr
            30              35                  40

TAC GAG TCG GCC GTC GGC AAC GCC GAG AGC CGC TAC GTC CTG ACC GGT       295
Tyr Glu Ser Ala Val Gly Asn Ala Glu Ser Arg Tyr Val Leu Thr Gly
            45              50                  55

CGT TAC GAC AGC GCC CCG GCC ACC GAC GGC AGC GGC ACC GCC CTC GGT       343
Arg Tyr Asp Ser Ala Pro Ala Thr Asp Gly Ser Gly Thr Ala Leu Gly
        60              65              70

TGG ACG GTG GCC TGG AAG AAT AAC TAC CGC AAC GCC CAC TCC GCG ACC       391
Trp Thr Val Ala Trp Lys Asn Asn Tyr Arg Asn Ala His Ser Ala Thr
75              80              85                  90

ACG TGG AGC GGC CAG TAC GTC GGC GGC GCC GAG GCG AGG ATC AAC ACC       439
Thr Trp Ser Gly Gln Tyr Val Gly Gly Ala Glu Ala Arg Ile Asn Thr
            95              100                 105

CAG TGG CTG CTG ACC TCC GGC ACC ACC GAG GCC AAC GCC TGG AAG TCC       487
Gln Trp Leu Leu Thr Ser Gly Thr Thr Glu Ala Asn Ala Trp Lys Ser
            110             115                 120

ACG CTG GTC GGC CAC GAC ACC TTC ACC AAG GTG AAG CCG TCC GCC GCC       535
Thr Leu Val Gly His Asp Thr Phe Thr Lys Val Lys Pro Ser Ala Ala
            125             130                 135

TCC ATC GAC GCG GCG AAG AAG GCC GGC GTC AAC AAC GGC AAC CCG CTC       583
Ser Ile Asp Ala Ala Lys Lys Ala Gly Val Asn Asn Gly Asn Pro Leu
            140             145                 150

GAC GCC GTT CAG CAG TAGTCGCGTC CCGGCACCGG CGGGTGCCGG GACCTCGGCC       638
Asp Ala Val Gln Gln
155
```

(2) INFORMATION FOR SEQ ID NO: 2:

(i) SEQUENCE CHARACTERISTICS:
        (A) LENGTH: 183 amino acids
        (B) TYPE: amino acid
        (D) TOPOLOGY: linear (xi) SEQUENCE DESCRIPTION: SEQ ID NO: 2:

```
Met Arg Lys Ile Val Val Ala Ala Ile Ala Val Ser Leu Thr Thr Val
-24             -20             -15                 -10

Ser Ile Thr Ala Ser Ala Ser Ala Asp Pro Ser Lys Asp Ser Lys Ala
            -5              1               5

Gln Val Ser Ala Ala Glu Ala Gly Ile Thr Gly Thr Trp Tyr Asn Gln
        10              15              20

Leu Gly Ser Thr Phe Ile Val Thr Ala Gly Ala Asp Gly Ala Leu Thr
25              30              35                  40

Gly Thr Tyr Glu Ser Ala Val Gly Asn Ala Glu Ser Arg Tyr Val Leu
            45              50                  55

Thr Gly Arg Tyr Asp Ser Ala Pro Ala Thr Asp Gly Ser Gly Thr Ala
```

```
                        60                 65                 70
Leu Gly Trp Thr Val Ala Trp Lys Asn Asn Tyr Arg Asn Ala His Ser
        75                  80                  85

Ala Thr Thr Trp Ser Gly Gln Tyr Val Gly Ala Glu Ala Arg Ile
        90                  95                 100

Asn Thr Gln Trp Leu Leu Thr Ser Gly Thr Thr Glu Ala Asn Ala Trp
105                 110                 115                 120

Lys Ser Thr Leu Val Gly His Asp Thr Phe Thr Lys Val Lys Pro Ser
                125                 130                 135

Ala Ala Ser Ile Asp Ala Ala Lys Lys Ala Gly Val Asn Asn Gly Asn
                140                 145                 150

Pro Leu Asp Ala Val Gln Gln
        155

(2) INFORMATION FOR SEQ ID NO: 3:

(i) SEQUENCE CHARACTERISTICS:
        (A) LENGTH: 604 base pairs
        (B) TYPE: nucleic acid
        (C) STRANDEDNESS: double
        (D) TOPOLOGY: linear (ix) FEATURE:
        (A) NAME/KEY: CDS
        (B) LOCATION:44..499
        (D) OTHER INFORMATION:Positions 44..115 correspond
            to sig peptide and 116..499 to mat peptide (xi) SEQUENCE DESCRIPTION: SEQ ID NO: 3:

GAATTCCGCA AGGAGCACAC CCGGCTGTCC ACCTGCTGCA GAG ATG GTG CAC GCA       55
                                                Met Val His Ala
                                                -24

ACC TCC CCG CTG CTG CTG CTG CTG CTC AGC CTG GCT CTG GTG GCT          103
Thr Ser Pro Leu Leu Leu Leu Leu Leu Ser Leu Ala Leu Val Ala
-20                 -15                 -10                 -5

CCC GGC CTC TCT GCC AGA AAG TGC TCG CTG ACT GGG AAA TGG ACC AAC      151
Pro Gly Leu Ser Ala Arg Lys Cys Ser Leu Thr Gly Lys Trp Thr Asn
                    1               5                   10

GAT CTG GGC TCC AAC ATG ACC ATC GGG GCT GTG AAC AGC AGA GGT GAA      199
Asp Leu Gly Ser Asn Met Thr Ile Gly Ala Val Asn Ser Arg Gly Glu
            15                  20                  25

TTC ACA GGC ACC TAC ATC ACA GCC GTA ACA GCC ACA TCA AAT GAG ATC      247
Phe Thr Gly Thr Tyr Ile Thr Ala Val Thr Ala Thr Ser Asn Glu Ile
        30                  35                  40

AAA GAG TCA CCA CTG CAT GGG ACA CAA AAC ACC ATC AAC AAG AGG ACC      295
Lys Glu Ser Pro Leu His Gly Thr Gln Asn Thr Ile Asn Lys Arg Thr
45                  50                  55                  60

CAG CCC ACC TTT GGC TTC ACC GTC AAT TGG AAG TTT TCA GAG TCC ACC      343
Gln Pro Thr Phe Gly Phe Thr Val Asn Trp Lys Phe Ser Glu Ser Thr
                65                  70                  75

ACT GTC TTC ACG GGC CAG TGC TTC ATA GAC AGG AAT GGG AAG GAG GTC      391
Thr Val Phe Thr Gly Gln Cys Phe Ile Asp Arg Asn Gly Lys Glu Val
            80                  85                  90

CTG AAG ACC ATG TGG CTG CTG CGG TCA AGT GTT AAT GAC ATT GGT GAT      439
Leu Lys Thr Met Trp Leu Leu Arg Ser Ser Val Asn Asp Ile Gly Asp
        95                  100                 105

GAC TGG AAA GCT ACC AGG GTC GGC ATC AAC ATC TTC ACT CGC CTG CGC      487
Asp Trp Lys Ala Thr Arg Val Gly Ile Asn Ile Phe Thr Arg Leu Arg
110                 115                 120

ACA CAG AAG GAG TGAGGATGGC CCCGCAAAGC CAGCAACAAT GCCGGAGTGC          539
Thr Gln Lys Glu
```

125

TGACACTGCT TGTGATATTC CTCCCAATAA AGCTTTGCCT CAGACAAAAA AAAAAAAGG        599

AATTC        604

(2) INFORMATION FOR SEQ ID NO: 4:

(i) SEQUENCE CHARACTERISTICS:
        (A) LENGTH: 152 amino acids
        (B) TYPE: amino acid
        (D) TOPOLOGY: linear (xi) SEQUENCE DESCRIPTION: SEQ ID NO: 4:

Met Val His Ala Thr Ser Pro Leu Leu Leu Leu Leu Ser Leu
-24              -20              -15              -10

Ala Leu Val Ala Pro Gly Leu Ser Ala Arg Lys Cys Ser Leu Thr Gly
            -5                    1                5

Lys Trp Thr Asn Asp Leu Gly Ser Asn Met Thr Ile Gly Ala Val Asn
            10                  15                  20

Ser Arg Gly Glu Phe Thr Gly Thr Tyr Ile Thr Ala Val Thr Ala Thr
25                  30                  35                  40

Ser Asn Glu Ile Lys Glu Ser Pro Leu His Gly Thr Gln Asn Thr Ile
                45                  50                  55

Asn Lys Arg Thr Gln Pro Thr Phe Gly Phe Thr Val Asn Trp Lys Phe
            60                  65                  70

Ser Glu Ser Thr Thr Val Phe Thr Gly Gln Cys Phe Ile Asp Arg Asn
            75                  80                  85

Gly Lys Glu Val Leu Lys Thr Met Trp Leu Leu Arg Ser Ser Val Asn
            90                  95                  100

Asp Ile Gly Asp Asp Trp Lys Ala Thr Arg Val Gly Ile Asn Ile Phe
105                 110                 115                 120

Thr Arg Leu Arg Thr Gln Lys Glu
                125

(2) INFORMATION FOR SEQ ID NO: 5:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO: 5:

CATGGCCGAA GCTGGTATCA CTGGGACCTG GTATAACCAA TGGGGG        46

(2) INFORMATION FOR SEQ ID NO: 6:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO: 6:

TCGACCCCCA TTGGTTATAC CAGGTCCCAG TGATACCAGC TTCGGC        46

(2) INFORMATION FOR SEQ ID NO: 7:

(i) SEQUENCE CHARACTERISTICS:
        (A) LENGTH: 59 base pairs
        (B) TYPE: nucleic acid
        (C) STRANDEDNESS: single (D) TOPOLOGY: linear (xi) SEQUENCE DESCRIPTION: SEQ ID NO: 7:

GCGCCATGGC CGAAGCTGGT ATCACTGGCA CCTGGTATAA CCAACTGGGG CGCACTTTC        59

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 8:

CGCGAAGCTT CAGCTGTCAT TAGCTA        26

(2) INFORMATION FOR SEQ ID NO: 9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 9:

GACGGAGCTC TGACTGGGAC CTACGAACGC GCGGTTGGTA        40

(2) INFORMATION FOR SEQ ID NO: 10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 10:

GACGGAGCTC TGACTGGCAC CTACGAATGG GCGGTTGGTA        40

(2) INFORMATION FOR SEQ ID NO: 11:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO: 11:

TTTCCATGCA TTCGCTTCGG TAGTGCCGGA TGTCCACAGC CACTGAGTG        49

(2) INFORMATION FOR SEQ ID NO: 12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 12:

GACGGAGCTC TGACTGGCAC CTACGAATAT GCGGTTGGTA        40

(2) INFORMATION FOR SEQ ID NO: 13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 13:

GCGAAATCGA CA                                                           12

(2) INFORMATION FOR SEQ ID NO: 14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 14:

ACTAGTGTCG ATTTCGCTGC AT                                                22

(2) INFORMATION FOR SEQ ID NO: 15:

(i) SEQUENCE CHARACTERISTICS:
        (A) LENGTH: 384 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..384

(xi) SEQUENCE DESCRIPTION: SEQ ID NO: 15:

```
ATG GCC GAA GCT GGT ATC ACT GGC ACC TGG TAT AAC CAA CTG GGG TCG           48
Met Ala Glu Ala Gly Ile Thr Gly Thr Trp Tyr Asn Gln Leu Gly Ser
    130                 135                 140

ACT TTC ATT GTG ACC GCT GGT GCT GAC GGA GCT CTG ACT GGC ACC TAC           96
Thr Phe Ile Val Thr Ala Gly Ala Asp Gly Ala Leu Thr Gly Thr Tyr
145                 150                 155                 160

GAA TCT GCG GTT GGT AAC GCA GAA TCC CGC TAC GTA CTG ACT GGC CGT          144
Glu Ser Ala Val Gly Asn Ala Glu Ser Arg Tyr Val Leu Thr Gly Arg
                165                 170                 175

TAT GAC TCT GCA CCT GCC ACC GAT GGC TCT GGT ACC GCT CTG GGC TGG          192
Tyr Asp Ser Ala Pro Ala Thr Asp Gly Ser Gly Thr Ala Leu Gly Trp
            180                 185                 190

ACT GTG GCT TGG AAA AAC AAC TAT CGT AAT GCG CAC AGT GCC ACT ACG          240
Thr Val Ala Trp Lys Asn Asn Tyr Arg Asn Ala His Ser Ala Thr Thr
        195                 200                 205

TGG TCT GGC CAA TAC GTT GGC GGT GCT GAG GCT CGT ATC AAC ACT CAG          288
Trp Ser Gly Gln Tyr Val Gly Gly Ala Glu Ala Arg Ile Asn Thr Gln
    210                 215                 220

TGG CTG TTA ACA TCC GGC ACT ACC GAA GCG AAT GCA TGG AAA TCG ACA          336
Trp Leu Leu Thr Ser Gly Thr Thr Glu Ala Asn Ala Trp Lys Ser Thr
225                 230                 235                 240

CTA GTA GGT CAT GAC ACC TTT ACC AAA GTT AAG CCT TCT GCT GCT AGC          384
Leu Val Gly His Asp Thr Phe Thr Lys Val Lys Pro Ser Ala Ala Ser
                245                 250                 255
```

(2) INFORMATION FOR SEQ ID NO: 16:

(i) SEQUENCE CHARACTERISTICS:
        (A) LENGTH: 128 amino acids
        (B) TYPE: amino acid
        (D) TOPOLOGY: linear (xi) SEQUENCE DESCRIPTION: SEQ ID NO: 16:

```
Met Ala Glu Ala Gly Ile Thr Gly Thr Trp Tyr Asn Gln Leu Gly Ser
  1               5                  10                  15

Thr Phe Ile Val Thr Ala Gly Ala Asp Gly Ala Leu Thr Gly Thr Tyr
```

-continued

```
                    20                    25                    30
Glu  Ser  Ala  Val  Gly  Asn  Ala  Glu  Ser  Arg  Tyr  Val  Leu  Thr  Gly  Arg
          35                         40                         45

Tyr  Asp  Ser  Ala  Pro  Ala  Thr  Asp  Gly  Ser  Gly  Thr  Ala  Leu  Gly  Trp
     50                         55                         60

Thr  Val  Ala  Trp  Lys  Asn  Asn  Tyr  Arg  Asn  Ala  His  Ser  Ala  Thr  Thr
65                       70                         75                         80

Trp  Ser  Gly  Gln  Tyr  Val  Gly  Gly  Ala  Glu  Ala  Arg  Ile  Asn  Thr  Gln
               85                         90                         95

Trp  Leu  Leu  Thr  Ser  Gly  Thr  Thr  Glu  Ala  Asn  Ala  Trp  Lys  Ser  Thr
                    100                        105                       110

Leu  Val  Gly  His  Asp  Thr  Phe  Thr  Lys  Val  Lys  Pro  Ser  Ala  Ala  Ser
          115                        120                       125
```